United States Patent
Bruno et al.

(10) Patent No.: US 10,265,126 B2
(45) Date of Patent: Apr. 23, 2019

(54) CARLO-COMPUTER ASSISTED AND ROBOT GUIDED LASER-OSTEOTOME

(75) Inventors: Alfredo E. Bruno, Basel (CH);
Hans-Florian Zeilhofer, Basel (CH);
Philipp Jürgens, Weil am Rhein (DE)

(73) Assignee: ADVANCED OSTEOTOMY TOOLS—OT AG, Basel (CH)

( * ) Notice: Subject to any disclaimer, the term of this patent is extended or adjusted under 35 U.S.C. 154(b) by 435 days.

(21) Appl. No.: 13/497,520

(22) PCT Filed: Sep. 22, 2009

(86) PCT No.: PCT/EP2009/006828
§ 371 (c)(1),
(2), (4) Date: Mar. 21, 2012

(87) PCT Pub. No.: WO2011/035792
PCT Pub. Date: Mar. 31, 2011

(65) Prior Publication Data
US 2012/0220992 A1  Aug. 30, 2012

(51) Int. Cl.
*A61B 18/20* (2006.01)
*A61B 34/30* (2016.01)
(Continued)

(52) U.S. Cl.
CPC ............ *A61B 18/20* (2013.01); *A61B 34/30* (2016.02); *A61B 34/32* (2016.02); *A61B 17/1657* (2013.01); *A61B 2017/00061* (2013.01); *A61B 2017/00694* (2013.01); *A61B 2018/00565* (2013.01); *A61B 2018/00601* (2013.01); *A61B 2018/00636* (2013.01); *A61B 2034/2055* (2016.02); *A61B 2090/062* (2016.02)

(58) Field of Classification Search
CPC ...... A61B 17/1657; A61B 2017/00061; A61B 2017/00694; A61B 19/2203; A61B 2019/162; A61B 2019/5255; A61B 18/20; A61B 2018/00636
USPC .............................................. 606/9; 600/595
See application file for complete search history.

(56) References Cited

U.S. PATENT DOCUMENTS 6,165,170 A * 12/2000 Wynne et al. ................... 606/9
6,395,000 B1 * 5/2002 Mitchell et al. ............... 606/15
(Continued)

FOREIGN PATENT DOCUMENTS

DE 102 20 423 A1 12/2003
WO WO 02/076302 A2 10/2002
(Continued)

OTHER PUBLICATIONS

Repprecht et al., "Sensor-based laser ablation for tissue specific cutting: an experimental study", Aug. 12, 2004, Lasers in Medical Science, col. 19: pp. 81-88.*

(Continued)

*Primary Examiner* — Boniface N Nganga
(74) *Attorney, Agent, or Firm* — Hickman Palermo; Becker Bingham LLP; Malgorzata A. Kulczycka

(57) ABSTRACT

A Computer Assisted and Robot-Guided Laser Osteotome (CARLO) medical device (1) for perforating hard tissue, having a photoablation laser source (31) mounted in a robotic arm (2), and optical system (37) for focusing a laser beam in a target plane of the ostetomy line featuring an autotracking navigation system (8).

15 Claims, 2 Drawing Sheets

(51) Int. Cl.
  *A61B 34/32* (2016.01)
  *A61B 17/16* (2006.01)
  *A61B 17/00* (2006.01)
  *A61B 18/00* (2006.01)
  *A61B 34/20* (2016.01)
  *A61B 90/00* (2016.01)

(56) References Cited

U.S. PATENT DOCUMENTS

| | | | |
|---|---|---|---|
| 6,451,010 B1* | 9/2002 | Angeley | 606/17 |
| 6,607,524 B1* | 8/2003 | LaBudde et al. | 606/10 |
| 6,621,060 B1* | 9/2003 | Nantel et al. | 250/201.4 |
| 7,288,086 B1 | 10/2007 | Andriasyan | |
| 8,753,332 B2* | 6/2014 | Bragagna et al. | 606/13 |
| 2006/0007965 A1* | 1/2006 | Tankovich et al. | 372/10 |
| 2006/0100498 A1* | 5/2006 | Boyce | A61B 6/505 600/408 |
| 2007/0060917 A1* | 3/2007 | Andriasyan | 606/10 |
| 2008/0033410 A1* | 2/2008 | Rastegar et al. | 606/9 |
| 2008/0215181 A1* | 9/2008 | Smith et al. | 700/245 |
| 2008/0255445 A1* | 10/2008 | Neubauer et al. | 600/416 |
| 2009/0227998 A1* | 9/2009 | Aljuri et al. | 606/13 |
| 2010/0049117 A1* | 2/2010 | Bragagna et al. | 604/20 |
| 2010/0274087 A1* | 10/2010 | Diolaiti et al. | 600/118 |
| 2011/0040287 A1* | 2/2011 | Ference et al. | 604/542 |

FOREIGN PATENT DOCUMENTS

| | | |
|---|---|---|
| WO | WO 2005/072657 A1 | 8/2005 |
| WO | WO 2007/038975 A1 | 4/2007 |
| WO | WO 2007/101015 A1 | 9/2007 |
| WO | WO 2009053499 A1 * | 4/2009 |
| WO | WO 2009138459 A1 * | 11/2009 ........... A61B 18/203 |

OTHER PUBLICATIONS

Kahrs, "Image processing aided laserknochenablation at the human petrous bone" Dessertation Feb. 12, 2009.*
European Patent Office, "International Search Report", in PCT/EP2009/006828, dated Jan. 7, 2010, 3 pages.
European Patent Office, "Search Report" in application No. 09 778 650.3, dated Oct. 2, 2015, 3 pages.
European Claims in application No. 09 778 650.3, dated Oct. 2015, 3 pages.
Office Action in application No. 16 181 542.8, dated Mar. 23, 2018, 3 pages.
Lüder Alexander Kahrs, "Bilverarbeitungsunterstutzte Laserknochenablation am humanen Felsenbein", dated Feb. 12, 2009, pp. 64-127, with English Translation.

* cited by examiner

CARLO-COMPUTER ASSISTED AND ROBOT GUIDED LASER-OSTEOTOME

TECHNICAL FIELD

The present invention relates to an automated Computer Assisted and Robot-Guided laser osteotome (CARLO) according to the preamble of independent claim 1. Such medical device can be used for cutting, drilling and milling bone and cartilage tissues to perform all forms of osteotomies in the field of craniomaxillofacial (CMF), orthopaedic, skullbase and dentoalveolar surgeries including dental implantology.

BACKGROUND ART

Osteotomies are currently performed with mechanical tools such as oscillating saws, chisels or drills. The precision in the cut, drilling or milling in the bones and cartilages obtained with these tools is limited by the size of the instrument used and only simple cutting geometries can be performed with these tools. An inherent drawback of using mechanical tools for osteotomy is that they are in direct contact with the hard tissue transmitting unwanted vibrations to the patient and, the heat generated by frictions, degrades the otherwise obtainable precision in the osteotomy.

Taking advantage of laser ablation methods of wide use in the micromachining of non-biological materials such as metals and plastics for replication and fast prototyping a new method to perform contact-free osteotomies is emerging offering distinct advantages over mechanical methods (see e.g. Kuttenberger J J., Stübinger S., Waibel A., Werner M., Klasing M., Ivanenko M., Hering P., Von Rechenberg B., Sader R., and Zeilhofer H F., *Photomed Laser surg.*, 2008 April; 26(2):129-36 and references herein). However, an important difference is encountered when micromachining biological tissues of patients by photoablation, as compared with e.g. metals or plastics, which contributed to delays in its development for osteotomic purposes, is the difficulty to properly fix the anatomical target of the patient to be operated. This difficulty precludes that the precision of the intervention be dominated by the size of the beam waist (the size of the laser beam at its focal point) but by the movements and vibrations of the invention overcomes such difficulty in the preferred embodiment by the use of a novel auto-tracking correcting tool which constantly compensate for the movements and vibrations of the anatomical part being operated.

Another possible reason accounting for delays in the implementation of laser micromachining of biological tissues is that laser micromachining of non-biological materials was justified from a commercial perspective because it is primarily used for the replication of parts (e.g. as in the auto industry) whereas in osteotomy every intervention is unique. However, modern imaging techniques of hard and soft tissues combined with fast prototyping methods for preoperative planning, as used in the present invention, facilitates the individual design step justifying now the use of laser micromachining for individual cases. Moreover, the use of these modern techniques becomes imperative for complicated cases.

The interaction of laser light with hard tissues, which is the first step in order to obtain efficient photoablation, has been studied in great detail using various types of lasers as shown in various clinical studies. In biological context, the term "photoablation" and derivations thereof as used herein refers to the vaporization of water in human tissues and its subsequent ejection induced by pulsed laser irradiation of selected wavelengths, specific powers and pulse durations. The deposited electromagnetic energy is almost entirely transformed into mechanical energy and the illuminated region is ejected at high velocity in the form of debris. The deposited energy is thus removed by the ejected debris precluding or minimizing the dissipation of heat minimizing thus thermal damage into the surface of the remaining tissue of significant relevance for the healing process.

Bone materials consist approximately of 13% water, 27% collagen and 60% hydroxyapatite and calcium phosphate. The mineral component of bone material is found in the form of hydroxyapatite crystallites, which is a form of calcium phosphate. The crystallites are surrounded by amorphous calcium phosphate and embedded in a collagen matrix. They reach a maximum size of 50 nm and are clustered along the collagen fibrils in distances of 60-70 nm; the clusters size up to a few micrometers. The melting point of the minerals is about 1500° C. Because the spectral characteristics of bone tissues are dominated by the absorption spectrum of water, the lasers that are known to efficiently photoablate bone and cartilage tissue are $CO_2$ gas lasers lasing at 10.6 μm, solid state Erbium lasers lasing at wavelengths of 2.94 μm and 2.79 μm (depending on the type of gain media), Holmium lasers lasing at 2.08 μm, Excimer lasers lasing at wavelengths shorter than 300 nm (Yow L., Nelson J. S. and Berns M. W., *Laser Surg., Med.;* 1989, 9, 141-147) solid state lasers Q-switched lasers with pulse widths of a few nanoseconds of various emitting wavelengths and, ultrafast femtosecond lasers (e.g. Girard B., Cloutier M., Wilson D J., Clokie C M., Wilson B V., *Laser. Surg. Med.,* 2007 June; 39(5): 458-67). The two most used lasers are however pulsed $CO_2$ and Erbium lasers. Erbium lasers have shown some advantages (see e.g. Stübinger S., Nuss K., Landes C., von Rechenberg B., and Sader R. *Laser Surg. Med.,* 2008 July; 40(5):312-8) over $CO_2$ lasers in terms of cutting precision and thermal damage. The higher precision observed in cuttings performed by Er:YAG (Erbium:yttrium aluminum garnet) lasers is primarily due to the fact that the absorption coefficient of liquid water is higher at 2.94 μm (of $12 \times 10^3$ cm$^{-1}$) than at 10.6 μm (of $0.7 \times 10^3$ cm$^{-1}$) resulting in short optical penetration by explosive vaporization. With pulses from free-running Er:YAG lasers this photoablation process is very efficient resulting in substantial ablation yields of 0.6 mm³/J with minimal thermal damage of about 10-15 μm in depth. In contrast, $CO_2$ lasers remove bone tissue by heating it up to the vaporization point and pyrolysis resulting in extensive char formation (i.e. carbonization) translating in delayed healing. Erbium lasers are thus more appropriate than $CO_2$ lasers and are used in the preferred embodiment of the present invention.

Laser cuttings have been done by directing the laser beam using e.g. fiber optical tips (Stübinger S., Landes C., Seitz O., and Sader R.; *J. Periodontol.* 2007 December, 78(12): 2389-94), with the help of laser beam manipulators controlled either by a joystick operated by the surgeon or, by means of a computer controller where the predefined cutting path such as the split line in a craniomaxillofacial (CMF) surgery, referred herein as the osteotomy line, has been previously programmed while the surgeon monitors the intervention. The manipulators used in the most advanced devices are based on XY deflecting mirrors (Kuttenberger J J., Stübinger S., Waibel A., Werner M., Klasing M., Ivanenko M., Hering M., Von Rechenber B., Sader R., Zeilhofer H F.; 2008 April; 26(2): 129:36). Sophisticated cuts have been achieved by mounting the beam focusing elements in this computer controlled optical scanner. Such optical delivery system is however best suitable to cut relatively flat bones because the beam scanner is fix with respect to the anatomical target and the beam waist cannot follow the complex curved bone tomography as those encountered in e.g. CMF surgery. Another problem associated with the use of manipulators based on XY moving mirrors is that the scanner is fixed and the distance from the focusing lens to the photoablation spots changes along the osteotomy line; i.e. it does not account for changes in the Z axis (coaxial to laser beam). This problem becomes serious when the osteotomy line is relatively large when using XY mirror scanners because the precision varies along the osteotomy line; i.e. it degrades when the beam waist is not at the target. It is thus desirable to have a means to ensure that the beam waist is always positioned at the spot to be photoablated. Besides the lack of control of the Z axis these XY beam deflectors do not allow for the control of the striking angle of the laser beam, defined by the angles $\Theta$ and $\Omega$ with respect to the tissue to be photoablated, required to augment the complexity in the cutting geometries or, required to avoid features such as a nerve or a tooth. In the preferred embodiment of the present invention the laser head of a compact solid state laser is mounted into the last segment of a robot-guided arm having several degrees of freedom which is capable of positioning the laser beam waist along the entire osteotomy line at any convenient striking angle. In another embodiment of the invention, this problem is solved by using an automatic autofocus system which ensures that the beam waist always lies on the desired place of the target, e.g. on the surface of the bone.

The precision of osteotomy has been greatly improved by the use of Operative Planning and Surgical Navigation methods from Computer Assisted Surgery (CAS) used to perform several types of complex interventions. Very important to CMF osteotomy is the possibility to have prior to the intervention a 3D representation of the anatomical region to be operated obtained nowadays by modern scanning technologies. These scannings are nowadays done by a number of available medical imaging technologies including CT (Computer Tomography), MRI (Magnetic Resonance Imaging), X-Rays, Ultrasound etc. Furthermore, different scanning methods can also be combined to obtain the final 3D dataset using fusion techniques. The final 3D dataset reproduces the exact geometrical situation of the normal and pathological tissues or particular structures of the region of interest. Artificial color contrast of the 3D dataset provides details of e.g. soft vs. hard tissue structures, allowing thus a computer to differentiate, and visually separate, different tissues and structures and, to prevent vulnerable anatomical structures from damage.

The 3D dataset reproducing the anatomical region of interest often includes intentional landmark features which are useful to realign the virtual dataset against the actual anatomy during surgery for navigation purposes. Different surgical guides, or headframes, to be attached to the patient's head for oral and CMF osteotomies have been developed. Optical positioning systems based on an infrared (IR) camera and various transmitters attached to e.g. the skull for CMF interventions offer distinct advantages to mechanical surgical guides. These are also positioned in convenient regions of the neurocranium and, in some cases, also in the instrument used to cut the bone. At least three IR transmitters attached in the neurocranium area are needed to compensate for the movements of the patient's head. In practice more than five transmitters are used to improve the precision, more preferentially more than seven transmitters are convenient. The 3D position of each transmitter is measured by the IR camera, using the same principle as used in satellite navigation. The workstation of the surgical navigator is constantly visualizing the actual position of the free-moving bone structures or fragments which are compared with the predetermined target position. In this way the bony fragments from the osteotomy can be accurately positioned into the target position a-priori determined by surgical simulation. In the preferred embodiment of the present invention an optical positioning navigation system is used in such way that its output feeds a novel auto-tracking correcting system connected to the robot-guided arm constantly compensates for the movements and vibrations in the anatomical part being operated to ensure that the actual cutting accurately corresponds to the predetermined target osteotomic line.

In another embodiment, a set of IR emitters is attached to the robot-guided arm where the photoablation laser is mounted to enhance the precision and safety of the instrument.

Summarizing, in contrast to mechanical methods, state-of-the-art photoablation methods offers the possibility to perform osteotomies with the following advantages:
a) Non-contact almost vibrationless interventions.
b) Higher precision.
c) Decreased bleeding.
d) Reduced postoperative period due to faster healing.
e) Possibility to perform complex cutting geometries.
f) Easy combination with available Surgical Navigation methods and Operative Planning.
g) Constant control the depth in the cutting, drilling or grinding of bone and cartilage to minimize or completely avoid damage in vulnerable structures (e.g. vessels and nerves) and the surrounding soft tissue However, there are a few remaining recognized issues which precludes its wide use to benefit a large segment of patients. Some of the drawbacks in osteotomies performed with state-of-the-art devices are:
a) Lack of an auto-tracking method to lock the coordinate system of the osteotomy line to the anatomical part of the patient being operated which is independent of the movements of the patient to precisely perform a pre-defined cutting path.
b) The limited degree of freedom in the manipulation systems to properly direct the photoablation laser beam to the osteotomy line.
c) The slow speed in the manipulation of the laser beam waist over the osteotomy line.
d) The lack of a system capable of removing photoablation gases and particles causing odor and distributing pathogenic particles into the operating theater.
e) Lack of safety features to stop the photoablation process by the surgeon in eventual emergency situations.

There is thus a need for a CARLO medical device which addresses the above mentioned deficiencies capable of faster and safely performs a predefined cutting geometry at various traversing angles at a constant precision which is independent from the movements of the patients and evacuates the photoablation debris and odor.

DISCLOSURE OF THE INVENTION

According to the invention these needs are settled by a CARLO for cutting, drilling and milling bone and cartilage tissue as it is defined by the features of independent claim 1. Preferred embodiments are subject of the dependent claims. In particular, the preferred embodiment of the present invention deals with a CARLO comprising basically of a computer console to control a compact solid state photoablation laser mounted in a robotic arm featuring a dedicated patient-photoablation laser autotracking system.

In the present invention the cutting of hard tissue with a pulsed laser is performed by drilling an array of adjacent holes equally spaced by a given pitch following a pre-defined path in a scanning fashion. Each individual hole is drilled by multiple laser shots in a given spot until the hard tissue is fully perforated when the laser irradiation is stopped. The laser beam is next re-positioned by the robotic arm to illuminate the next spot in the predetermined osteotomy line to drill the adjacent hole in the same way. This process is repeated until the complete pre-defined osteotomy line has been cut.

The osteotomy line is defined by a photoablation dataset comprising a linear array of spots containing both, the position of the spots where each hole is to be perforated and, the striking angle of the photoablation beam of the beam with respect to the bone surface. The position of each spot is defined by a set of X, Y and Z values and, the striking angle is defined by a set of angles, $\Theta$ and $\Omega$. The photoablation dataset contains thus the XXZ-$\Theta\Omega$ information of every hole in the osteotomy line. The 3D dataset of the anatomical region of interest is previously gathered preferably by MRI but it could be obtained by other tomographic methods such CT, X-Rays, Ultrasound etc. or, by a combination from some of these methods whereas the photoablation dataset has to be designed by the surgeon or an expert using the 3D dataset and computer modeling software. The photoablation dataset and the 3D dataset of the anatomical region of interest are stored in the CARLO in the same coordinate system.

A preferred laser source is a solid state pumped Er:YAG laser lasing a 2.94 µm. There are two types of Er:YAG lasers depending on the pumping source of the gain media that could be used in conjunction with the CARLO. The Er:YAG laser used in osteotomy reported in the prior art is pumped by conventional flash lamps operating at repetition frequencies lower than 50 Hz and most commonly lasing between 5 Hz and 20 Hz with pulses having a temporal line width of 150 to 300 µsec and most commonly around 250 µsec where the laser is operated in free-running mode; i.e. with no pulse shortening devices such a Q-switch. In the preferred embodiment of the present invention we use an Er:YAG laser pumped by laser diodes (LD) referred thereafter as LD-Er:YAG laser. LD-Er:YAG laser are more efficient than flash pumped Er:YAG lasers in terms of energy conversion, can be operated at a much faster repetition rate and are smaller facilitating its integration into a robotic arm. Preferably, one or more LD are used to pump the laser gain media. Preferably, pulses having temporal widths of less than 250 microseconds and, most preferably, below 50 µsec are achieved with a LD-Er:YAG laser. The pulse repetition frequency of the photoablation laser source preferably is higher than 200 Hz, most preferably higher than 500 Hz provided that the temporal width and energy of each pulse is capable to induce efficient photoablation.

The cooling of the laser gain media of either the LD pumped or the flash lamp pumped Er:YAG laser could be done by air flow from a propeller or, by a separate circulating liquid system to ensure that the laser operates at a constant temperature to avoid or minimize beam degradation during the operation due to thermal fluctuations as e.g. due to thermal lensing. However, in another embodiment, the running temperature of the Erbium laser and/or the LD could be controlled by means of a thermoelectric temperature controller featuring, e.g., Peltier elements and a thermocouple sensor as described by A. Bruno et. al. in *Anal. Chem.* 63(23), p. 2689 (1991). Such active temperature controller would allow a comparably easy miniaturization of the photoablation laser facilitating its integration into a robotic arm.

Another critical parameter in clinical practice is the shortening of the whole treatment time for a procedure which is achieved in the present invention by using a laser operating at repetition rates above 50 Hz, preferably above 200 Hz, most preferably above 500 Hz. Repetition rates above 200 Hz allow the drilling of individual holes with multiple pulses in a very short period of time. Also, to achieve an overall short treatment time, other processes contributing to the overall duration of the treatment have to be fast such as, e.g., the re-positioning of the laser beam from one spot to the next by the robotic arm and, the time devoted to stop and re-start the laser after drilling each hole by e.g. electronic or mechanical means as explained further below. Therefore, in the preferred embodiment of this invention all processes contributing to the overall duration of the treatment are automated and the laser head is mounted in a very fast and compact robotic arm. Under such conditions the total time to drill a hole should be a few sec; e.g. 3 sec. For example, to cut an osteotomy line of one cm requiring fifty (50) holes with the CARLO when 3 sec are needed to drill each hole including all additional tasks such as repositioning the robotic arm etc. about 2 min are needed.

A key issue when drilling the individual holes is the control of in the depth of each hole which preferably should not perforate the soft tissue in contact with the hard tissue; i.e. the photoablation process should stop immediately after the hole is traversed. This is of particular importance in CMF surgery of bilateral mandibular sagittal-split osteotomy for correction of CMF deformities. The split line in these osteotomies usually traverses the mandibular canal where the inferior alveolar nerve is located and this is at great risk of injury during laser corticotomy. In the preferred embodiment of the present invention the CARLO features a closed-loop control system to stop the laser sending laser pulses at the hard-soft tissue interface when the bone I fully traversed. This is achieved in the preferred embodiment by means of e.g. an optoacoustic sensor capable of differentiating a change in the acoustic signal generated by each laser pulse during the photoablation when the tissue is hard or soft or by timing the echo triggering the optical laser pulse with e.g. an infrared photodiode and detecting a pressure change due to the sound propagating in the tissue by e.g. a piezoelectric accelerometer (Rupprecht S., Tangerman-Gerk K., Schultze-Mosgau S., Neukan F. W., and Enrich J.; Lasers Surg. Med.; 2005, 36:168-192).

Thereby, the acoustical sensor preferably comprises sound evaluating means. With such sound evaluating means changes in sound characteristics e.g. caused by single laser pulses on the tissue surface, can be detected and analysed. Such changes in sound characteristics can be changes in the acoustic impedance of the tissue or in the frequency pattern or, in the amplitude of the sound wave.

Considering that the changes in the tissue thickness over the photoablation path are usually smooth, dedicated software can be used to, e.g., store the number of pulses from the previously drilled hole or holes to speed up the overall process using a dedicated algorithm. Furthermore, with these dedicated software the characteristic of an individual hole can be compared with the predetermined value such as, e.g., an acoustic waveform or a fluorescence at a given wavelength and, laser pulses illuminating the individual hole can be stopped when the characteristic of the individual hole match the predetermined value. Also, the accuracy in the stopping of the drilling of individual holes can be improved by the smooth decrease in the power of the laser pulses after e.g. perforating 80% of the hole as estimated from the number of pulses used to perforate the previous hole. Thus, the drilling closed-loop feed-back unit allows ensuring a comparably comfortable, fast, and efficient perforation of the bone.

In another embodiment the depth of the hard tissue to be photoablated is determined using a new, noninvasive, optical signal acquisition and processing imaging technology called Optical Coherent Tomography (OCT). OCT allows extremely high-quality, micrometer-resolution, three-dimensional images from within optical scattering media of biological tissue. In contrast to other optical methods, OCT, an interferometric technique typically employing near-infrared light, is able to penetrate significantly deeper into the scattering medium. Depending on the use of high-brightness and wide-spectrum light sources such as superluminescent diodes or ultrashort pulse lasers, OCT has achieved sub-micrometer resolution (with very wide-spectrum sources emitting over a ~100 nm wavelength range). A relatively recent implementation of OCT, frequency-domain OCT, provides advantages in signal-to-noise ratio and therefore faster signal acquisition.

In a further preferred embodiment, the closed-loop control system comprises an optical sensor. Such an optical sensor can have a measurement system such as a fluorescence detector, an interferometer or an optical coherence tomography instrument. Thereby, the optical sensor preferably comprises color evaluating means. With such an optical sensor a change of color of the bottom of the hole can be detected and analyzed. Since the color of the bone usually differs from the color of the bone in which situation the drilling process in this specific hole is stopped. Thus, such color evaluating means allow an efficient control of the drilling process.

In a preferred embodiment, the CARLO comprises a debris capture system with a e.g. vacuum pump, a coarse filter and a fine particle filter for evacuating debris and removing odor. The first coarse filter and derivations thereof as used herein relates to a mechanical filter being capable of retaining comparably large particles and could be realized by, e.g., glass wool or glass fibers. Such a filter entraps particles in the range of 1 micrometer up to 1 millimeter, preferably 30 micrometer to 500 micrometer. The term "fine filter" and derivations thereof as used herein relates to a component containing chemically active substances, such as, e.g., active coal particles, and a lower mesh membrane embedded in, e.g., glass wool or glass fiber or any other supporting porous structure to filter odor producing particles and possible pathogens from escaping the CARLO into the operating theater. Indeed, such fine filter is meant to entrap molecules and particles in the range of 0.010 μm up to 100 μm, preferably 1 μm to 50 μm. Most conveniently, the coarse filter is placed before the fine filter in the sense of the air flow and debris stream coming from the bone. Thereby, the pump preferably is connected by means of plastic tubes with the coarse filter and the fine filter. In a preferred embodiment the coarse filter and the fine filter are combined into a disposable single filter unit to be used only once per patient.

By removing the debris from the bone as described above, the optical components of the CARLO can be kept clean near the bone being treated during the whole photoablation process by means of an aspirating nozzle and filters. Thus, contamination of the focusing optics of the CARLO is avoided or reduced to retain constant photoablation efficiency through the whole treatment which is otherwise compromised by a decrease in the transmission of the optics when dirty. The benefits of a debris capture module is thus that pathogens, molecules and particles can be retained within the CARLO allowing a reduction of odor produced by the photoablation of the bone, keep debris away from the optics of the CARLO and protecting the patient, surgeon, nurses etc. in the operating theater from pathogens.

The stopping of the laser illumination after the hole is traversed and, its re-starting to drill the adjacent hole, can be done either by electronic means that stop laser action in the laser head or, by means of a fast mechanical shutter or an optical diaphragm located anywhere along the beam optical path Thereby, the optical path of the photoablation laser beam is always jacketed inside the CARLO for enhanced optical safety of the CARLO since the shutter or the diaphragm can be otherwise closed, e.g., when the laser head is warming up.

The CARLO has a component to visualize the operation as it proceed in the monitor of the computer console while the image is being captured by e.g. a CCD or an analogue video camera mounted also in the last stage of the robotic arm. This feature allows the surgeon to stop the automatic photoablation process at any point by e.g. closing the mechanical shutter and the movements of the robot. This is primarily a safety feature which could be used by the surgeon to verify if the operation proceeds as planned or, if the surgeon decides to continue the operation manipulating the robotic arm by means of e.g. a joystick.

Summarizing the present invention, the CARLO employs a laser beam mounted in a robotic arm to create, by means of fast photoablation, a pre-determined and array of holes of pitch in bones or cartilages to cut an osteotomic line or for milling a given bone area or, to drill individual holes to screw mounting plates or for dental implants. Prior to the laser osteotomy several preoperative tasks have to be performed to program the CARLO with all the information required including the 3D dataset of the anatomic area of interest and the photoablation dataset as well as the positioning of all the optoelectronic navigation devices for the proper functioning of beam-patient autotracking system. Preferably, the laser beam delivers light having a wavelength of 2.94±0.2 micrometer but it could also emit radiation at other wavelengths where water has strong absorption bands.

Thus, the present invention results in a significant improvement from prior art by addressing issues relevant to the patients and surgeon without jeopardizing the safety of the treatment in question. Such relevant issues include higher osteotomic precision, enhanced safety, short treatment duration, small ergonomic design suitable for point-of-care treatments, sophisticated debris evacuation system which inhibits odor and prevent pathogens in the photoablation debris to escape into the operating theater, acoustic isolation resulting in minimal amount of noise, a means to stop the laser of drilling individual holes before the whole bone is traversed to prevent the damage of adjacent soft tissue.

BRIEF DESCRIPTION OF THE DRAWINGS

The laser osteotome according to the invention is described in more detail herein below by way of exemplary embodiments and with reference to the attached drawings, in which.

MODE(S) FOR CARRYING OUT THE INVENTION

Figure 1:
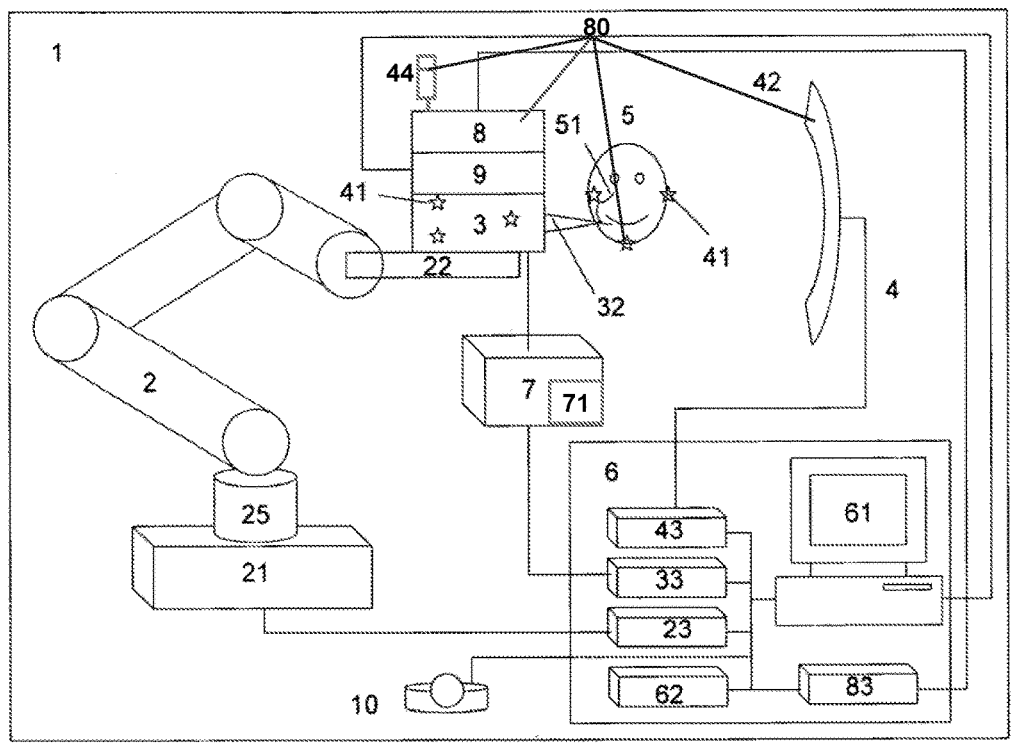
FIG. 1 shows a schematic view of a first embodiment of a modular CARLO medical device according to the invention having several modules.

FIG. 1 shows a possible configuration of a CARLO medical device (1) as used in a CMF operation with the head of a patient (5), the robotic arm (2), the autotracking navigation system (4), the photoablation laser head unit (3) and evacuation supply system unit (7), the central operating console (6) with the joystick (10).

The central operating console (6) contains the navigation autotracking interface unit (43), the photoablation laser and evacuation driving unit (33), the robot interface unit (23), the autotracking sensor interface unit (83) as well as the osteotomy design unit (62).

The robotic arm (2) has several degrees of freedom to be able to position the laser beam (32) to any desired position of the osteotomy line (51) and at any desired angle. The base of the robotic arm (25) is mounted in a flat linear or curved positioning module (21) to make the adjustments and calibrations needed prior to the operation. The last segment of the robotic arm is a platform (22) where the laser head unit (3), the image capturing elements (9), the IR emitters (41) and the IR antenna (42) and the sensors (8) of the closed loop drilling system (80).

Figure 2:
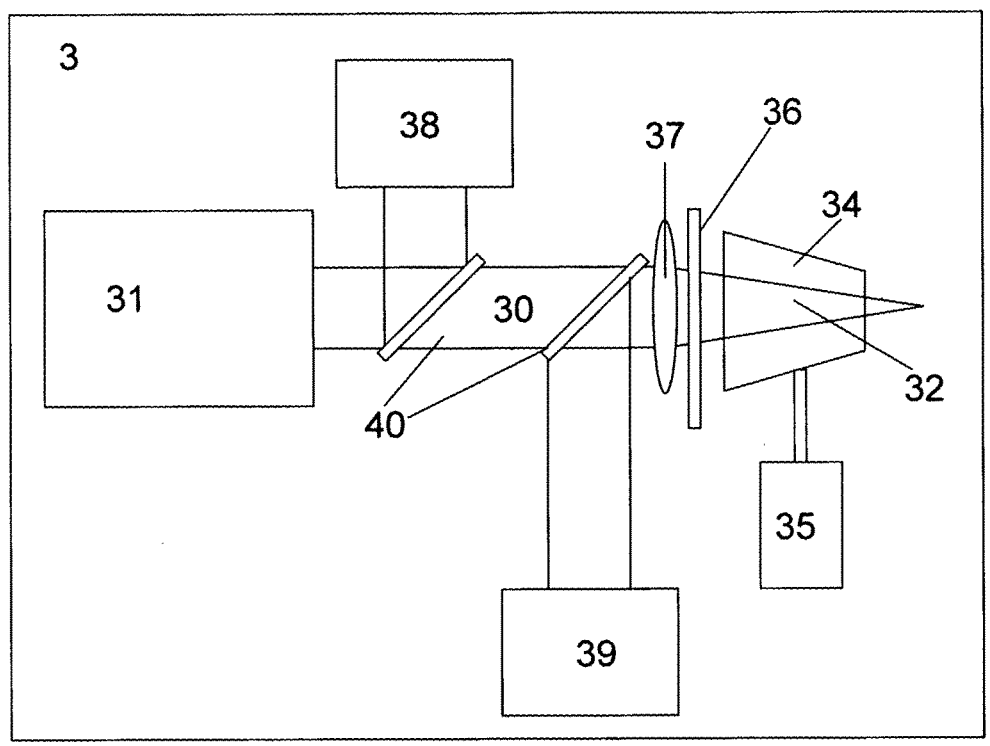
FIG. 2 shows a schematic view of the preferred arrangement of the laser head unit of the CARLO.

FIG. 2 shows the laser head unit (3) containing the photoablation laser (31), the focused (32) and the collimated (30) parts of the laser beam, the beam focusing optics (37), a transparent window (36) to prevent debris to contaminate the focusing optics (37) connected to an aspirating nozzle (34) and to an to an aspirating pump (71) located preferably in the laser and evacuation supply system unit (7), a photodiode (38) from the closed loop hole depth control system (80), two beam splitters (40) and an optical detector (39).

The photoablation laser (31) should emit at wavelengths where water has strong absorption bands and is preferably selected from the group of Erbium solid state lasers such as: Er:YAG, Er/Pr:YAG, Ho:YAG, Er/Cr:YSGG. Holmium solid state lasers such as:Ho/Nd:YAG or Ho:YSGG. Diode lasers, fiber lasers, or any other laser capable to photoablate the bone tissue and where the output wavelength is not otherwise harmful to the human body can also be used in the CARLO. The photoablation laser (31) has a pulse temporal width which is between 10 femtoseconds and 1 millisecond, preferably, between 10 nanosecond and 300 microsecond. The photoablation laser (31) also delivers an energy density of a laser beam between 1 millijoule per square centimeter and 100,000 joule per square centimeter, in particular, between 10 millijoule per square centimeter and 5 joule per square centimeter.

The lenses of the optical element (37) have a fixed configuration with a beam waist range in the focal plane of a few millimeters preferably about 4 millimeters allowing accurate perforation also of curved bones without focus adjustment. Alternatively, an optical autofocusing element is incorporated into the beam focusing optics (37) comprising at least one lens that can change its distance with respect to the surface of the bone to ensure that the waist of the focused laser beam strikes the bone on its surface or at a specified level inside the bone.

The debris and odor disposable filter (35) is conveniently arranged in the laser head unit (3) to be easily disposable to avoid cross-contamination of different diseases in different patients and, it is connected to an aspirating pump (71) preferably located in the laser and evacuation supply system unit (7).

The closed loop hole depth control system (80) requires an acoustical sensor and (44), a time triggering element which could be a photodiode (38) and an electronic processing unit or computer (61).

The central operating console (6) comprises the computer (61) running the dedicated software to control all functions of the CARLO medical device (1) by means of various interface units. Included functions are the robotic arm (2), the Photoablation Laser (31), and the autotracking navigation system (4).

The invention also covers all further features shown in the figures individually although they may not have been described in the afore or following description.

While the invention has been described with particular reference to certain embodiments thereof, it will be understood that changes and modifications may be made by those of ordinary skill within the scope and spirit of the following claims. In particular, the present invention covers further embodiments with any combination of features from different embodiments described above and below.

The invention claimed is:

1. An automated computer assisted and robotic guided laser osteotome (CARLO) medical device to photoablate human hard tissues to facilitate surgical interventions, the CARLO medical device comprising:
   a) a photoablation laser source;
   b) a robotic arm for precisely positioning a photoablation laser beam into a target osteotomic line;
   c) a laser head unit comprising the photoablation laser source;
   d) a stored photoablation dataset, the photoablation dataset predefining the target osteotomic line and comprising an array of spots including positions of the spots where holes are to be perforated and striking angles of the photoablation laser beam with respect to a bone surface;
   e) a central operating console adapted to automatically drive the robotic arm over the target osteotomic line, control the photoablation laser source of the laser head unit to employ the photoablation laser beam configured to perforate holes according to the photoablation dataset, and
   perform other controlling tasks;
   f) a navigation autotracking system configured to automatically correct the positions of the target osteotomic line with respect to the photoablation laser source; and
   g) a closed loop drilling system configured to control a depth of perforating individual holes in the bone surface along the target osteotomic line using a color composition of the individual holes.

2. The CARLO medical device of claim 1, wherein the photoablation laser source is a pulsed Erbium solid state laser.

3. The CARLO medical device of claim 1, wherein the laser source is a laser diode pulsed Erbium solid state laser.

4. The CARLO medical device of claim 1, wherein pulses of the laser source have temporal width between 10 femtoseconds to 300 seconds.

5. The CARLO medical device according to claim 1, wherein the closed loop drilling system is configured to stop the laser photoablation in a neighborhood of a ventral hard-to-soft tissue interface.

6. The CARLO medical device according to claim 5, wherein the closed loop drilling system comprises an acoustical sensor, a time triggering element and an electronic processing unit.

7. The CARLO medical device according to claim 5, wherein the closed loop drilling system comprises a high-resolution OCT system.

8. The CARLO medical device according to claim 5, wherein the closed loop system to control the depth of the individual holes features an optical sensor.

9. The CARLO medical device according to claim 8, wherein the optical sensor is capable of analyzing the color composition of the individual holes being evaluated.

10. The CARLO medical device according to claim 1, wherein a focusing optics of the laser source comprises an autofocus optical system.

11. The CARLO medical device according to claim 1, wherein the photoablation laser is operated manually by means of a joystick.

12. The CARLO medical device according to claim 1, wherein each of individual holes drilled in multiple shots is completed by shooting sequentially in the same spot until a hole is perforated.

13. The CARLO medical device according to claim 1, comprising a disposable particle filter connected to an aspirating nozzle and a aspirating pump to capture photoablation generated odorous molecules and debris.

14. The CARLO medical device according to claim 1, wherein the navigation autotracking system comprises a set of infrared emitters, an infrared antenna, and a set of data stored and processed in the central operating console to correct the position of the photoablation beam.

15. The CARLO medical device according to claim 14, wherein the set of infrared emitters is placed in the laser head unit.

* * * * *

UNITED STATES PATENT AND TRADEMARK OFFICE
CERTIFICATE OF CORRECTION

PATENT NO. : 10,265,126 B2  
APPLICATION NO. : 13/497520  
DATED : April 23, 2019  
INVENTOR(S) : Alfredo E. Bruno et al.

Page 1 of 1

It is certified that error appears in the above-identified patent and that said Letters Patent is hereby corrected as shown below:

On the Title Page

Item [73] Assignee: delete "Advanced Osteotomy Tools – OT AG" and insert -- Advanced Osteotomy Tools – AOT AG --.

Signed and Sealed this  
Ninth Day of July, 2019

Andrei Iancu  
*Director of the United States Patent and Trademark Office*